US007422692B1

(12) United States Patent
Sanders

(10) Patent No.: US 7,422,692 B1
(45) Date of Patent: Sep. 9, 2008

(54) RAW INFLUENT TREATMENT PROCESSES ELIMINATING SECONDARY BIOLOGICAL TREATMENT

(76) Inventor: Launeil Neil Sanders, 2206 Canaan Pointe Dr., Spartanburg, SC (US) 29306-6293

( * ) Notice: Subject to any disclaimer, the term of this patent is extended or adjusted under 35 U.S.C. 154(b) by 1140 days.

(21) Appl. No.: 09/699,318

(22) Filed: Oct. 30, 2000

Related U.S. Application Data

(63) Continuation-in-part of application No. 09/289,723, filed on Apr. 12, 1999, now abandoned.

(51) Int. Cl.
*C02F 1/56* (2006.01)
(52) U.S. Cl. .................. 210/709; 162/189; 210/711; 210/712; 210/725; 210/727; 210/743; 210/917; 210/928
(58) Field of Classification Search ............... 162/29, 162/189, 190; 210/620, 631, 702, 710, 711, 210/709, 721, 724, 726, 739, 743, 917, 928, 210/712, 725, 727; 422/79; 436/62
See application file for complete search history.

(56) References Cited

U.S. PATENT DOCUMENTS

| | | | | |
|---|---|---|---|---|
| 3,627,679 A | * | 12/1971 | Fuller | 162/29 |
| 3,945,917 A | * | 3/1976 | Foster | 162/29 |
| 3,997,439 A | * | 12/1976 | Ayukawa | 210/719 |
| 4,282,093 A | * | 8/1981 | Haga et al. | 210/101 |
| 4,724,045 A | * | 2/1988 | Ackel | 162/29 |
| 4,855,061 A | * | 8/1989 | Martin | 210/101 |
| 5,068,038 A | * | 11/1991 | Fischer et al. | 210/662 |
| 5,120,448 A | * | 6/1992 | Dorica et al. | 162/30.1 |
| 5,200,089 A | * | 4/1993 | Siefert et al. | 210/725 |
| 5,433,853 A | * | 7/1995 | Mamone | 210/615 |
| 5,766,485 A | * | 6/1998 | Lind et al. | 162/189 |
| 5,798,047 A | * | 8/1998 | Tekawa | 210/198.1 |
| 5,846,433 A | * | 12/1998 | Sorensen et al. | 210/709 |
| 6,491,827 B1 | * | 12/2002 | Temple et al. | 210/727 |

* cited by examiner

*Primary Examiner*—Peter A. Hruskoci

(57) ABSTRACT

Presently no chemicals are added in the pulp/paper mills wastewater treatment. There is a loop hole with the Biological Oxygen Demand test utilized. Regulators depend on the Biological Oxygen Demand test. All mills are discharging raw untreated wastes high in Chemical Oxygen Demand, (COD), Total Organic Carbon, (TOC) and COLOR. Liquid Alum solution is added to raw influent. All electrical energy aerated systems are eliminated. All flows from sewers join prior to the entrance to clarifier. The continuous in-line pH controller is proprietary as well as the continuous in-line COD analyzer. Because mills wastewater is amphoteric, it is mandatory that the raw influent pH be adjusted to range of 5.7 to 6.0 for optimum removal efficiencies. Aluminum chloride, ferric chloride and ferrous sulfate may be replaced for alum with higher operating costs. The precipitate is thickened, dewatered and incinerated, and approximately 75% of the chemicals regenerated.

4 Claims, 3 Drawing Sheets

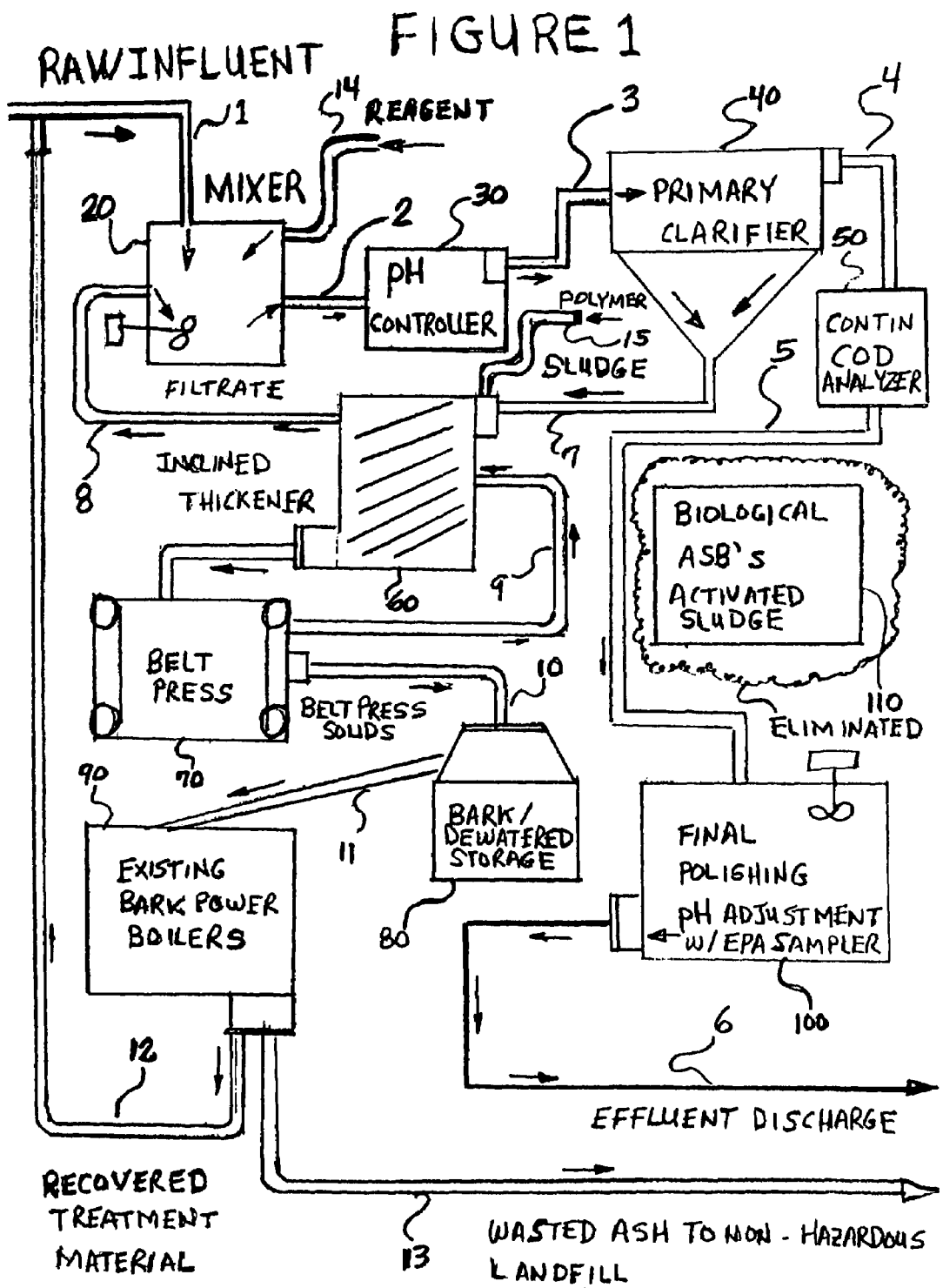

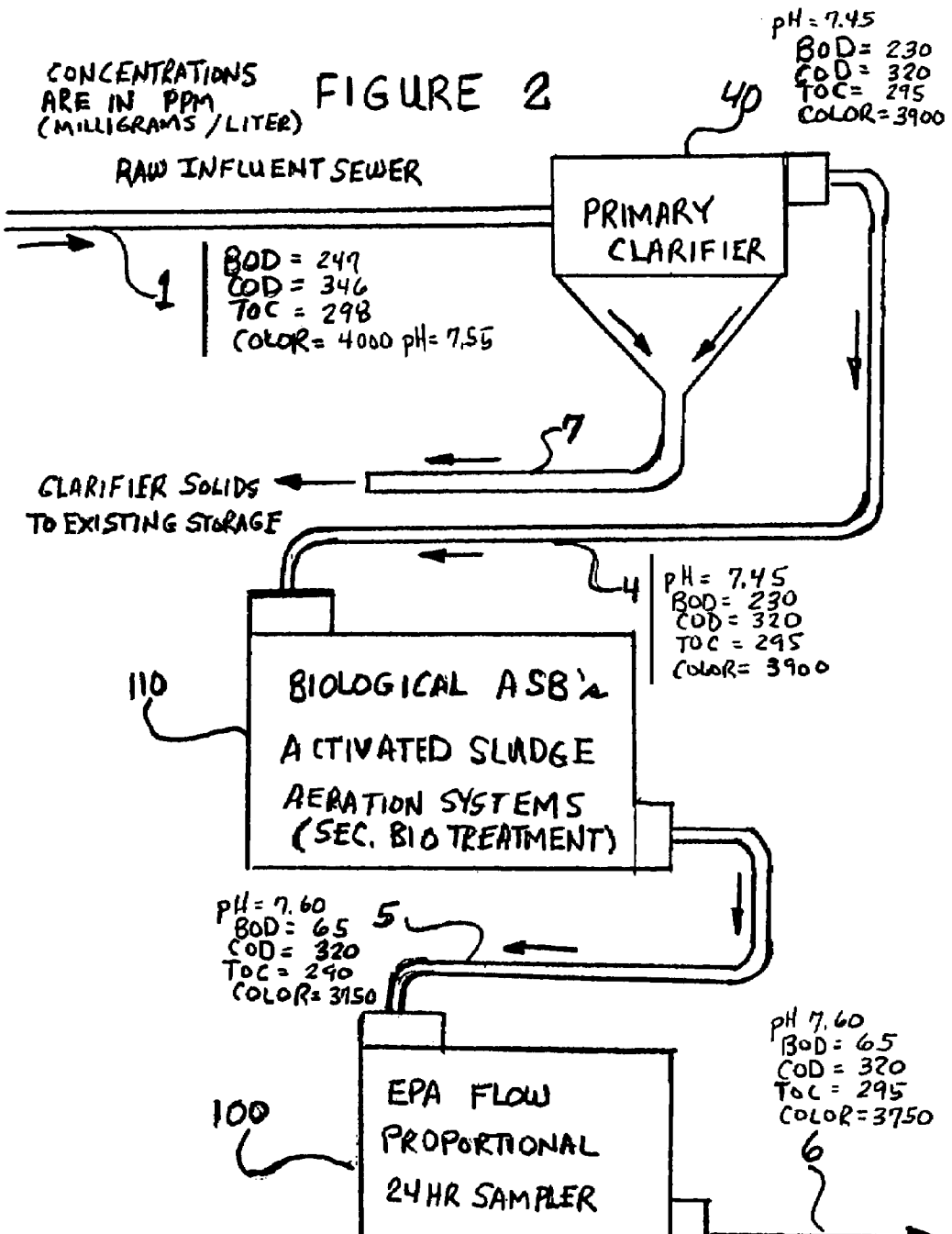

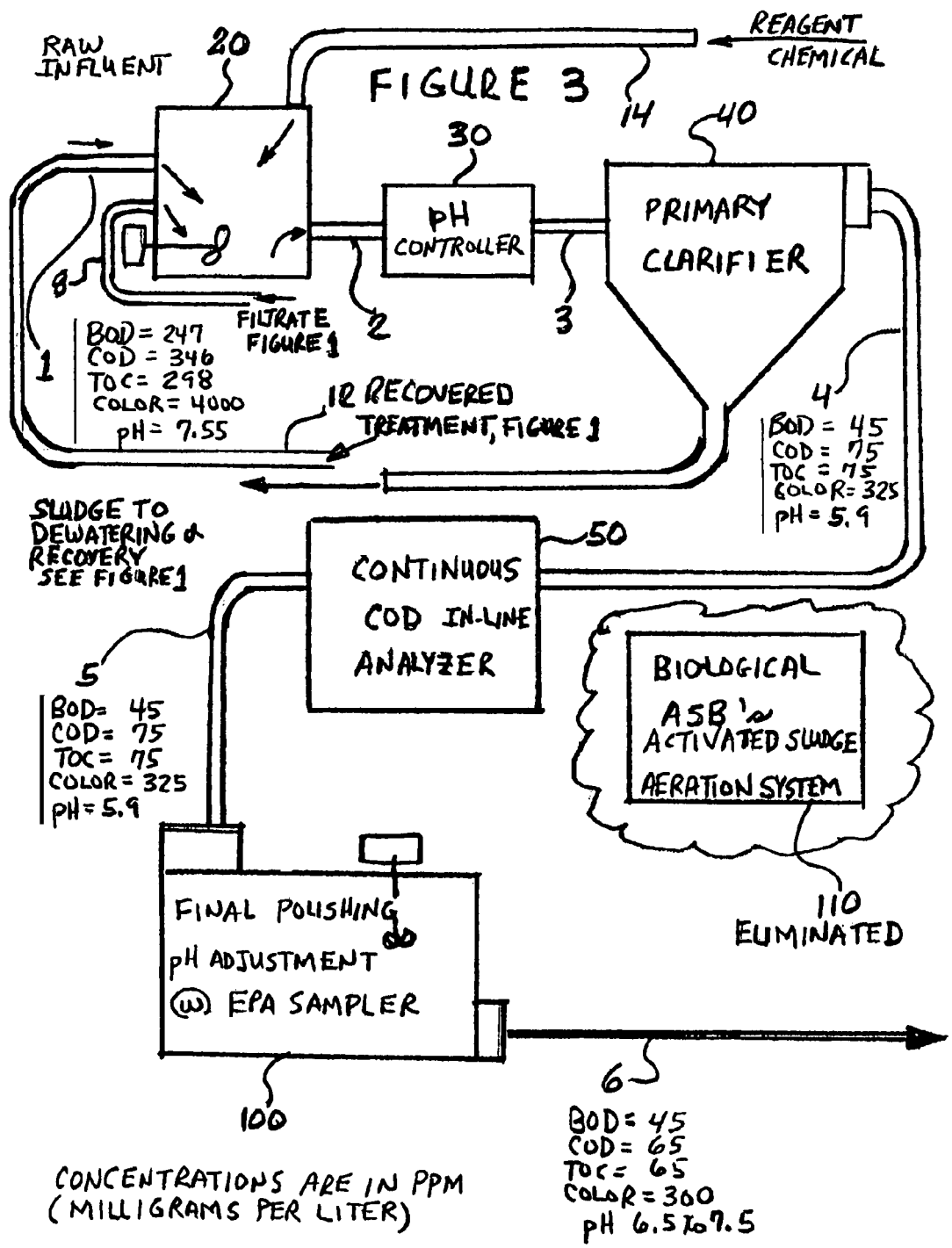

RAW INFLUENT TREATMENT PROCESSES ELIMINATING SECONDARY BIOLOGICAL TREATMENT

CROSS-REFERENCE TO RELATED APPLICATIONS

This is a continuation-in-part of Ser. No. 09/289,723 filed on Apr. 12, 1999, now abandoned.

STATEMENT REGARDING FEDERALLY SPONSORED RESEARCH OR DEVELOPMENT

"Not Applicable"

REFERENCE TO A MICROFICHE APPENDIX

"Not Applicable"

BACKGROUND OF THE INVENTION

1. Field of Invention

This invention relates to paper making processes, pulping mills and manufacture at fully integrated pulp and paper mills and to raw influent treatment processes for reducing Chemical Oxygen Demand, Total Organic Carbon, and Color in these raw influent streams in production of pulp and paper; and it does have other applicability to other industrial and municipal Publicly Owned Treatment Works (POTW) effluent treatment. Secondary biological treatment is eliminated.

2. Description of Prior Art

Large amounts of water are used in various stages of the pulping, bleach plant, and papermaking processes. At the DeRidder, La., mill of Boise Cascade where I was Corporate Environmental Engineer the average raw influent wastewater flow was 30 million gallons per day. The paper making processes such as at Boise's mill included bark removal, pulping digesters, chlorine, hypochlorite, and caustic extraction operations in bleach plant, three combination power boilers, chemical recovery boiler, lime kiln, groundwood, and thermomechanical pulping. Boise's DeRidder, La., mill discharged an average of 30 to 37.5 million gallons per day of wastewater to a small low flow stream Anacoco Bayou.

The raw influent wastewater stream 1, in FIG. 1, is contaminated with lignins, lignin degradation products, humic acids, and sulphates attached to ring structures, cellulose fibers, cooking chemicals and like. These contaminants make the effluent stream dark colored, and are often referred to as color bodies. Since pulp and paper mills produce large quantities of this densely colored raw influent, a discharge of this effluent into adjacent streams and bodies of water causes an objectionable discoloration of the water.

In 1985 the Best Available Control Technology (BACT) in Clean Water Act, Public Law 92-500, and National Pollutant Discharge Elimination System (NPDES) effluent guidelines had Color limits of 200 to 250 milligrams per liter concentration limits for Color. These proposed Color limits were eventually deleted. When this becomes fully vamped into the public domain and at EPA's leadership and industry's leadership, everyone wins. Industry will have immediately more expansion capacity capability at all their operating plants and will save tremendous amounts of electrical energy. Furthermore, streams accepting industries' wastewater will have extremely more assimilative capacity to accept wastes and protect human health and aquatic life.

FIG. 1 is a schematic representation of a typical integrated pulp and paper plant's wastewater treatment system, typical for Boise's DeRidder, La., mill. The raw influent stream 1, in FIG. 1, is the main influent sewer entering a clarifier. In all mills nationwide no chemicals are added, and only gravity settling is utilized. The average pH of raw influent is in range of 7.5 to 8.5; and this was true for Boise's DeRidder raw influent. Various processes have been proposed for decolorization at this stage; however all other state of art dictate that biological secondary treatment is additionally required. This invention is an improvement as it eliminates the secondary biological treatment. When this becomes into the public domain, other old art and patents already issued may be also commercialized. Additionally, all other prior art are that there is no biological degradation. In the United States there are approximately 950 pulp and paper mills where no chemicals are added at a clarifier. There is no change, no reduction in the Chemical Oxygen Demand, Total Organic Carbon, and Color across a clarifier and aerated secondary biological system, activated sludge, and all other biological aerated systems. All other old art were not aware that there was never, ever any biological degradation, destruction in secondary biological systems.

As in Fuller, U.S. Pat. No. 3,627,679 the inventor, states "the need for biological treatment of pulp and paper mill effluent has forced the art to include effluent disposal systems of greater or lesser efficacy as an almost integral part of a pulp and paper mill complex."

As in Siefert, et al, U.S. Pat. No. 5,200,089 the inventor states the following: "Once the suspended solids have been precipitated in basin 3, the effluent stream moves through channel 5 into bio-degradation basins 7 and 9. The pH of the stream entering the biodegradation basins 7 and 9 must be between pH 7 and 8 in order to prevent damage to microorganisms in the basins."

As in Ackel, U.S. Pat. No. 4,724,045 Ackel states the following: "and then on to be biologically treated 16 to remove BOD. Such biological treatment and the methods of biological treatment are well known in the art."

As in Lind, et al, U.S. Pat. No. 5,766,485 Lind, et al, states the following: "Suspended solids can be readily removed and organic materials that use up oxygen, that is, that have a high biochemical oxygen demand (BOD), can also be generally removed using existing technologies."

Thus, the inventions of Fuller, U.S. Pat. No. 3,627,679; Siefert, et al, U.S. Pat. No. 5,200,089; Ackel, U.S. Pat. No. 4,724,045 and Lind, et al, U.S. Pat. No. 5,766,485 may be commercialized more rapidly with the discovery of my invention that secondary biological treatment may be and shall be eventually eliminated.

However, as discussed and described in this invention that there are actually no biological treatment, no biological degradation and no bugs eating and degrading organics. Additionally, that the Biochemical Oxygen Demand test for these pulp and paper mill wastewater has some severe loop-holes and is detrimental to the environment and water quality. As noted in Lind, et al, U.S. Pat. No. 5,766,485, the inventor points out that Fuller process has not been adopted widely because of three reasons. In Lind, et al, U.S. Pat. No. 5,766,485 alum process residues (APR) were used to remove colored contaminants. However Lind, et al, U.S. Pat. No. 5,766,485 as well as Fuller, U.S. Pat. No. 3,627,679; Siefert, et al, U.S. Pat. No. 5,200,089; Newton, U.S. Pat. No. 4,201,666 and Ackel, U.S. Pat. No. 4,724,045 all considered that secondary biological aeration treatment could not be eliminated. And, as well, this was stated and known art of treatment in pulp and paper mills wastewater. The basic premise was, when I joined Boise's DeRidder Mill, even though the wastewater discharged had a Color concentration of 3000 to 5000 milligrams per liter, there wasn't anything harmful in the wastewater, and it would cost millions of dollars to clean the wastewater. Basic premise is "it is too expensive, and secondary biological treatment is satisfactory." Thus, I was told if we now spend $5,000,000 for biological treatment; it is not economically feasible to spend another $5,000,000 for Color Removal. However, with my discovery and the facts revealed that there are zero reduction of COD and TOC from secondary biological treatment, this basic premise fails. In reality, the 800 to 1000 milligrams per liter Chemical Oxygen Demand, the 300 to 600 milligrams per liter Total Organic Carbon, and the 2500 to 5000 milligrams per liter Color are being discharged to our nation's navigable waters. Therefore as well as all the other 900 integrated pulp and paper mills in the United States, there is no biological degradation taking place in the aerated stabilization basins, activated sludge, and all other aeration systems. This invention needs to become into "the public domain." It is imperative for the U.S. Environmental Protection Agency and all fifty states' environmental control agencies to immediately become aware of a loop hole in the Biological Oxygen Demand (five day test). There may become an urgency of revising all pulp/paper mills' NPDES wastewater permits to reflect new Chemical Oxygen Demand limits.

Conventional early treatment processes such as precipitation of the suspended solids with lime, polyelectrolyte polymers or inorganic metallic salts are effective in removing some color from such effluent. Some polyelectrolyte polymers at high dosage rates are prohibitively expensive and technically unfeasible for treating large quantities of wastewater generated by commercial size pulp and paper plants. Inorganic metallic salts produce a great deal of solids; however when secondary biological aeration treatment is eliminated there is a tremendous cost savings in electricity for the electrical aerators and maintenance of these aeration equipment. This will encourage commercialization of prior art and this invention. And in this invention, burning the dewatered solids in existing combination bark/oil/gas/coal fired combination boilers rewards the industry with credits for electrical energy saved by utilizing the resultant energy (BTU content) of the dewatered solids, plus the several annual millions of dollars saved annually by turning-off all electrical aeration equipment. Furthermore, the reduction and high removal efficiencies for Chemical Oxygen Demand and Total Organic Carbon across a clarifier renders this technology to be very cost-effective.

SUMMARY OF THE INVENTION

The invention obtains the above objects and advantages by providing raw influent treatment process eliminating secondary biological treatment and generating resultant cost savings to operators by eliminating aerators' horsepower and maintenance. This results in direct economic electrical energy savings in the United States and to the Worldwide Pulp and Paper industry. Additional advantages are that the Chemical Oxygen Demand (COD), Total Organic Carbon (TOC), and COLOR concentrations in the effluent are reduced by 90% to 95% directly resulting in improved water quality in our nation's streams and navigable waters. Specific and preferred embodiment of invention provides that there is really no biodegradation and no reduction in organics, Chemical Oxygen Demand, Total Organic Carbon, and Color in the secondary biological aeration systems; and that by elimination of secondary biological treatment, the addition of chemicals at a raw influent to a clarifier is economical. This raw influent treatment process provides for adding chemicals at combined influent in a clarifier with alum, aluminum chloride, ferric chloride, and ferrous sulfate as the more preferred chemicals.

In one preferred embodiment of the invention, optimum control and removal efficiencies for said Chemical Oxygen Demand, Total Organic Carbon, and Color are instituted by an continuous in-line pH controller of addition of said reagent chemicals which controls the large volumes of raw influent flow to a set pH of 5.7 to 6.0. Thus, the continuous in-line pH controller 30, in FIG. 1, operates by continuously measuring the pH in the sewer at stream 2, and it provides automatic feedback for alum control. This continuous in-line pH controller is proprietary and mandatory. In this preferred embodiment the chemical liquid alum, liquid aluminum chloride, liquid ferric chloride or liquid ferrous sulfate are pumped to the head of stream 2. The most preferred embodiment is that a continuous in-line pH controller controls the addition of reagent chemicals. The continuous in-line pH controller obtains 90-95% Biochemical Oxygen Demand, 90-95% Chemical Oxygen Demand, 90-95% Total Organic Carbon and 90-95% Color removal efficiencies across a clarifier. As proven in Boise Southern's DeRidder wastewater, and additionally from South Carolina Department of Health and Environmental Control, SCDHEC, files the 795 milligrams per liter Chemical Oxygen Demand, the 368 milligrams per liter Total Organic Carbon, and the 2820 milligrams per liter Color presently being discharged by Bowater, Catawba, S.C., mill would all be reduced to a high effluent quality.

According to a further preferred embodiment, the monitoring and controlling the Color, Chemical Oxygen Demand, and Total Organic Carbon removal efficiencies across a clarifier are enhanced by insertion of a continuous in-line Chemical Oxygen Demand analyzer at outlet of a clarifier. This continuous in-line Chemical Oxygen Demand analyzer 50, continuously measures the Chemical Oxygen Demand, COD, concentration in milligrams per liter. And there will be a correlative, removal efficiency tracking in the same 90% to 95% removal efficiencies for Total Organic Carbon, TOC, and Color if the continuous in-line pH controller is operating properly and controlling to the optimum pH set point of 5.7 to 6.0.

BRIEF DESCRIPTION OF THE DRAWINGS

FIG. 1 is schematic flow sheet showing the various stages of present raw influent treatment process.

FIG. 2 is schematic flow diagram depicting the Existing conventional biological treatment and loop holes in the Biochemical Oxygen Demand test. The flow sheet demonstrates the associated high COD, TOC, and Color concentrations discharged to streams and navigable waters.

FIG. 3 is schematic flow diagram depicting with this invention "Raw Influent Treatment Processes Eliminating Secondary Biological Treatment" and which demonstrates the improved low BOD, COD, TOC and Color concentrations with absolute elimination of secondary biological treatment.

DETAILED DESCRIPTION OF THE INVENTION

Description of the Preferred Embodiment

Main contention of the pulp and paper industry was Color removal by excess lime treatment and other chemicals would cost millions of dollars per year and any other Color technology process was not technically justified as it would be cost prohibitive. Raw influent wastewater from pulp and paper mills are very high colored (Color concentrations range from 2500 milligrams per liter to 5000 milligrams per liter) and are high in Chemical Oxygen Demand and Total Organic Carbon materials.

In a first step, the raw influent process sewer flows through line 1, in FIG. 1, into flash mixer 20 and are stirred, flash mixed together sequentially with Alum solution, and mixed with cationic or anionic polymer to absorb the color forming and organic bodies in the raw influent wastewater. The chemicals liquid Alum solution is controlled by continuous in-line pH controller from line 2 feeding into continuous in-line pH controller 30. After mixing in flash mixer for a few minutes residence time, the flow is transferred continuously through the continuous in-line pH controller in line 2. It exits the flash mixer in line 3 to a clarifier 40. In a clarifier the solids are further coagulated, agglomerated and settled out of solution. As in other known water treatment and wastewater treatment, the addition of cationic or anionic polymer increases the settling rate and eventual ease of thickening in order to produce higher dewatered solids going to bark pile storage. It also increases the BTU content of the dewatered sludge. The clarified supernatant from which the color bodies have been removed can be decanted through line 4 after specified settling time in clarifier design. At this supernatant discharge in line 4 from a clarifier, the Color has been reduced approximately by 90% to 98% to an average Color of 200 to 300 milligrams per liter. The supernatant is continuously analyzed by continuous in-line Chemical Oxygen Demand Analyzer, (COD) 50.

The solids remaining in a clarifier underflow tank bottom are recovered through line 7 and thickened in an inclined settler or similar thickener/settler 60 to remove more water increasing percent solids consistency. This water is removed through line 8 and is recycled back to mixer 20. The solids are further dewatered, as with standard available belt presses 70, to concentrate the solids further to approximately 25 percent to 35 percent. Water is drawn off in line 9 and recycled back to the inclined thickener 60. The fully dewatered solids can be conveyed from the belt presses via belt conveyor 10 onto the existing bark storage 80. The dewatered solids do have some BTU content and are mixed with existing bark and wood residues as they are conveyed from bark storage 80 to the existing power boilers via conveyor 11; thus dewatered solids are regenerated by burning in existing combination bark/oil/coal fired boilers 90.

The ash remaining from the existing combination bark/oil/coal fired boilers 90 is recycled back to raw influent process sewer through line 12 back to mixer 20. Through this line 12 the recovered chemical is solubilized and tied back into raw influent process line 1 reentering mixer. Because of the fact that some of the ash content are inerts, such as Calcium, Magnesium, Silica and other inerts (such as at Boise's DeRidder mill the inerts averaged approximately 20 percent); approximately 20 percent to 35 percent inerts are wasted to non-hazardous landfill through line 13.

Based on the test results approximately 65 percent of recovered the chemicals are available for re-use and for flocculation in line 1. Approximately 35% of new commercial Alum solution reagent would be added through reagent line 14.

Normally only one polymer utilizing a dosage rate of 0.25 to 3.00 parts per million is used in the mixer along with the liquid alum solution. This is would be an anionic. As in the DeRidder tests, this dosage rate of 0.25 to 3.00 parts per million of anionic polymer performed the best. A cationic polymer is added through line 15 to further increase solids consistency and concentration in inclined thickener 60.

The supernatant after passing through the in-line Chemical Oxygen Demand Analyzer 50 passes through line 5 onto final polishing tank, or in most cases will pass through existing aerated stabilization basins, aeration systems with aerators turned off. The supernatant will buffer on all occasions back up to pH of 6.5 to 7.5 because of the carbonate pick-up and available sodium ions in solution. (This was actually proven in 30 days trial at Boise's mill with full plant flow of 30 million gallons per day of Alum treatment at a primary clarifier; and with 23 days retention in Boise's aerated stabilization basins, the outlet pH was 7.5.) However, just as emergency safeguard in case Total Suspended Solids, TSS, or pH need to be adjusted, this final polishing tank 100 is added prior to final discharge in line 6 exiting the final polishing tank.

For the basic premise for which U.S. Environmental Protection Agency, EPA, and states regulatory agencies, and top line management at the pulp and paper companies rely on is as follows: "If we are spending $5,000,000 now for secondary biological treatment, then in no way can we justify spending another $5,000,000 for Color removal alone, as Color is not harmful and is only of aesthetic concern." However, I discovered in the discovery of my invention this is not true because of the loop hole in the Biological Oxygen Demand (BOD) test as previously discussed.

In a first step of existing current treatment, the raw influent process sewer flows through line 1, in FIG. 2, into the clarifier with no chemicals added at a clarifier 40. In a clarifier the solids are further coagulated, agglomerated and settled out of solution. Clarifier solids in a clarifier underflow are pumped through stream 7 to existing clarifier solids storage. The clarified supernatant is passed through line 4 to biological aerated stabilization basins or activated sludge systems 110 (secondary biological treatment) after specified settling time in clarifier design. Notice in FIG. 2, that negligible amounts of organic matter are removed across a clarifier without addition of chemicals. The supernatant exiting secondary biological treatment passes in line 5 through an EPA flow proportional continuous sampler 100 and discharges to the navigable stream or waters through line 6. In FIG. 2, it shows that the concentrations of COD, TOC and Color are relatively the same in the inlet stream 4 and outlet stream 5 of the aerated stabilization basins or activated sludge systems reflecting a loop hole in the biological oxygen demand test.

FIG. 3 is the new improved process same as FIG. 1, except FIG. 1 is more detailed as it shows the clarifier solids thickening, dewatering and incinerating in bark, oil, gas, or coal power boiler. FIG. 1 also shows regenerating a portion of chemicals and recycling to a flash mixer 20. In a first step, FIG. 3, the raw influent process sewer flows through line 1, in FIG. 3, into flash mixer 20 and are stirred, flash mixed together sequentially with Alum solution, and mixed with cationic or anionic polymer to absorb the color forming and organic bodies in the raw influent wastewater. The chemicals liquid Alum solution is controlled by continuous in-line pH controller from line 2 feeding into continuous in-line pH controller 30. After mixing in flash mixer for a few minutes residence time, the flow is transferred continuously through the continuous in-line pH controller in line 2. It exits the flash mixer in line 3 to a clarifier 40. In a clarifier the solids are further coagulated, agglomerated and settled out of solution. The clarified supernatant from which the color bodies have been removed can be decanted through line 4 after specified settling time in clarifier design. At this supernatant discharge in line 4 from a clarifier, the Color has been reduced approximately by 90% to 98% to an average Color of 200 to 300 milligrams per liter. The supernatant is continuously analyzed by continuous in-line Chemical Oxygen Demand Analyzer, (COD) 50.

The solids remaining in a clarifier underflow tank bottom are recovered through line 7 and thickened in an inclined settler or similar thickener/settler 60 to remove more water increasing percent solids consistency as shown in FIG. 1, a more detailed flow schematic.

The clarified supernatant is passed through line 4 to biological aerated stabilization basins or activated sludge systems 110 (secondary biological treatment). Here in FIG. 3 and FIG. 1, the supernatant passes through the aerated stabilization basins, activated sludge systems 110 with all of the aerators shut off since the organics have been removed in a clarifier with addition of chemicals. As an emergency safeguard in case Total Suspended Solids, TSS, or pH need to be adjusted, this final polishing tank 100 is added prior to final discharge in line 6 exiting the final polishing tank.

Alum is liquid available solution which is an aluminum sulfate. [$Al_2(SO_4)_3$]. This liquid Alum solution can be purchased from many manufacturers such as General Chemical, Van Waters and Rogers Chemical Corporation, American Cyanamid and others. This liquid alum has 17% active Di-aluminum Trioxide ingredient. Approximate bulk cost of the liquid alum solution is $125 per ton based on dry basis as Di-aluminum Trioxide.

Aluminum chloride [$AlCl_3$] is commercial grade liquid solution of aluminum chloride. The aluminum chloride also performs as well as the liquid Alum solution.

Ferric Chloride which is liquid solution [$FeCl_3$]; and Ferric Sulfate which is liquid solution [$Fe_2(SO_4)_3$] also may be utilized with similar COD, TOC, and Color removal efficiencies. Ferrous sulfate can be purchased in bulk in dry and solubilized in storage tank and fed via positive displacement metering pumps similar to the other chemicals. The continuous in-line pH controller is set at the set point, the optimum pH at 5.7 to 6.0 to achieve the greatest reductions in COD, TOC and Color.

Ferrous sulfate is a solid which can be solubilized as stated above and fed similar to all other chemicals pumped. [$Fe(SO_4) \cdot 7\frac{1}{2}H_2O$]. Probably the liquid alum liquid solution would be most economical as this liquid alum solution is utilized in paper machines head box and fiber mixing chambers prior to flowing onto paper machine screens moving at high speeds up to 3500 feet per minute. Thus, most mills already have storage facilities on plant premises of 17% Di-aluminum Trioxide solutions.

The invention claimed is:

1. A raw influent treatment process eliminating secondary biological treatment comprising:
 a) adding to raw influent a liquid alum solution in the dosage rates of 250 to 335 milligrams per liter;
 b) adding to raw influent a liquid alum solution with addition being continuously controlled by continuous in-line pH controller to pH of 5.7 to 6.0;
 c) adding to raw influent about 0.25 to 3.0 parts per million of an anionic polyelectrolyte polymer to increase settling rate, agglomeration and effectiveness of sedimentation and increase Color, Chemical Oxygen Demand and Total Organic Carbon removal efficiencies producing a supernatant liquid layer from which the color bodies and 95% of organics are removed;
 d) monitoring and controlling the Color, Chemical Oxygen Demand and Total Organic Carbon removal efficiencies across a clarifier by insertion of continuous in-line Chemical Oxygen Demand analyzer at outlet of a clarifier;
 e) separating the supernatant liquid layer from which the color bodies and organics have been removed in the clarifier;
 f) removing the solids from a clarifier underflow stream in the clarifier, dewatering the solids, incinerating the dewatered solids in a bark, oil, gas, or coal power boiler, regenerating of a portion of recovered metal ions from ash and wasting of some of dewatered solids up to approximately 20% to 35% depending on content, percentage, of inert boiler ash in the raw influent;
 g) passing the supernatant liquid layer onto other final polishing/pH adjustment, if needed, and since Chemical Oxygen Demand, Total Organic Carbon, and Color removal efficiencies are exceedingly high, greater than 95%, no biological treatment is required and secondary biological treatment is eliminated.

2. A raw influent treatment process eliminating secondary biological treatment comprising:
 a) adding to raw influent a liquid aluminum chloride solution in the dosage rates of 250 to 400 milligrams per liter;
 b) adding to raw influent a liquid aluminum chloride solution with addition being continuously controlled by continuous in-line pH controller to pH of 5.7 to 6.0;
 c) adding to raw influent about 0.25 to 3.0 parts per million of an anionic polyelectrolyte polymer to increase settling rate, agglomeration and effectiveness of sedimentation and increase Color, Chemical Oxygen Demand and Total Organic Carbon removal efficiencies producing a supernatant liquid layer from which the color bodies and 95% of organics are removed;
 d) monitoring and controlling the Color, Chemical Oxygen Demand and Total Organic Carbon removal efficiencies across a clarifier by insertion of continuous in-line Chemical Oxygen Demand Analyzer at outlet of a clarifier;
 e) separating the supernatant liquid layer from which the color bodies and organics have been removed in the clarifier;
 f) removing the solids from a clarifier underflow stream in the clarifier, dewatering the solids, incinerating the dewatered solids in a bark, oil, gas, or coal power boiler, regenerating of a portion of recovered metal ions from ash and wasting of some of dewatered solids up to approximately 20% to 35% depending on content, percentage, of inert boiler ash in the raw influent;
 g) passing the supernatant liquid layer onto other final polishing/pH adjustment, if needed, and since Chemical Oxygen Demand, Total Organic Carbon, and Color removal efficiencies are exceedingly high, greater than 95%, no biological treatment is required and secondary biological treatment is eliminated.

3. A raw influent treatment process eliminating secondary biological treatment comprising:
 a) adding to raw influent a ferric chloride liquid solution in the dosage rates of 250 to 425 milligrams per liter;
 b) adding to raw influent a ferric chloride liquid solution with addition being continuously controlled by continuous in-line pH controller to a pH of 5.7 to 6.0;
 c) adding to raw influent about 0.25 to 3.0 parts per million of an anionic polyelectrolyte polymer to increase settling rate, agglomeration and effectiveness of sedimentation and increase Color, Chemical Oxygen Demand and Total Organic Carbon removal efficiencies producing a supernatant liquid layer from which the color bodies and 95% of organics are removed;
 d) monitoring and controlling the Color, Chemical Oxygen Demand and Total Organic Carbon removal efficiencies across a clarifier by insertion of continuous in-line Chemical Oxygen Demand Analyzer at outlet of a clarifier;
e) separating the supernatant liquid layer from which the color bodies and organics have been removed in the clarifier;
f) removing the solids from a clarifier underflow stream in the clarifier, dewatering the solids, incinerating the dewatered solids in a bark, oil, gas, or coal power boiler, regenerating of a portion of recovered metal ions from ash and wasting of some of dewatered solids up to approximately 20% to 35% depending on content, percentage, of inert boiler ash in the raw influent;
g) passing the supernatant liquid layer onto other final polishing/pH adjustment, if needed, and since Chemical Oxygen Demand, Total Organic Carbon, and Color removal efficiencies are exceedingly high, greater than 95%, no biological treatment is required and secondary biological treatment is eliminated.

4. A raw influent treatment process eliminating secondary biological treatment comprising:
a) adding to raw influent a ferrous sulfate liquid solution in the dosage rates of 250 to 425 milligrams per liter;
b) adding to raw influent a ferrous sulfate liquid solution with addition being continuously controlled by continuous in-line pH controller to a pH of 5.7 to 6.0;
c) adding to raw influent about 0.25 to 3.0 parts per million of an anionic polyelectrolyte polymer to increase settling rate, agglomeration and effectiveness of sedimentation and increase Color, Chemical Oxygen Demand and Total Organic Carbon removal efficiencies producing a supernatant liquid layer from which the color bodies and 95% of organics are removed;
d) monitoring and controlling the Color, Chemical Oxygen Demand and Total Organic Carbon removal efficiencies across a clarifier by insertion of continuous in-line Chemical Oxygen Demand Analyzer at outlet of a clarifier
e) separating the supernatant liquid layer from which the color bodies and organics have been removed in the clarifier;
f) removing the solids from a clarifier underflow stream in the clarifier, dewatering the solids, incinerating the dewatered solids in a bark, oil, gas, or coal power boiler, regenerating of a portion of recovered metal ions from the ash and wasting of some of dewatered solids up to approximately 20% to 35% depending on content, percentage, of inert boiler ash in the raw influent;
g) passing the supernatant liquid layer onto other final polishing/pH adjustment, if needed, and since Chemical Oxygen Demand, Total Organic Carbon, and Color removal efficiencies are exceedingly high, greater than 95%, no biological treatment is required and secondary biological treatment is eliminated.

* * * * *